United States Patent [19]

Tollner

[11] 4,432,233

[45] Feb. 21, 1984

[54] APPARATUS FOR SIMULATING SOIL MECHANICAL IMPEDANCE ON ROOT GROWTH POTENTIAL

[75] Inventor: Earnest W. Tollner, Experiment, Ga.

[73] Assignee: The University of Georgia, Athens, Ga.

[21] Appl. No.: 391,833

[22] Filed: Jun. 24, 1982

[51] Int. Cl.³ .............................................. G01M 3/00
[52] U.S. Cl. .................................... 73/432 SD; 73/84
[58] Field of Search ........................ 73/84, 85, 432 SD

[56] References Cited

U.S. PATENT DOCUMENTS

| | | | |
|---|---|---|---|
| 3,906,781 | 9/1975 | Vlasblom | 73/84 |
| 3,968,682 | 7/1976 | Saint-Remy Pellissier | 73/84 |
| 4,061,021 | 12/1977 | Baldwin | 73/84 |

OTHER PUBLICATIONS

*Agricultural Engineering*, vol. 19, No. 2, Feb. 1938, "The Dynamic Properties of Soil; VIII, A Study of the Nature of Physical Forces Governing the Adhesion Between Soil and Metal Surfaces", Kummer and Nichols, pp. 3–8.
*Agronomy Journal*, Sep. 29, 1954, "Pfeffer's Studies of the Root Growth Pressures Exerted by Plants", Gill and Bolt, pp. 166–168.
*Soil Science*, vol. 108, No. 2, 1969, "Root Elongation Rates of Cotton and Peanuts as a Function of Soil Strength and Soil Water Content", Taylor and Ratliff, pp. 113–119.
*Plant Physiol.*, vol. 45, 1970, "Diurnal Variations in Root Diameter", Huck, Klepper and Taylor, pp. 529–530.
*Agriculture Handbook*, 316 U.S. Dept. of Agriculture, 1970, "Soil Dynamics in Tillage and Traction", Gill and Vanden Berg, pp. 180–183.
*ASAE*, 1971, "Compaction of Agricultural Soils", Barnes et al., pp. 70–73.
*Plant and Soil*, 36, 1972, "Soil Physical Conditions Affecting Seedling Root Growth", Eavis, pp. 613–622.
*ASAE*, vol. 18, No. 5, 1975, "Lubrication of Soil-Metal Interfaces", Schafer, Gill and Reaves, pp. 848–851.
*Agronomy Journal*, vol. 69, Sep.–Oct. 1977, "Measurement of Radish Root Enlargement Under Mechanical Stress", Kibreab et al., pp. 857–860.
"Plant Root Systems: Their Function and Interaction With the Soil", Russell, McGraw-Hill Book Company Ltd., 1977.
*ASAE*, No. 4, 1981, "Modifying the Root Environment to Reduce Crop Stress", Bowen, pp. 21–39.
*J. Agric. Engng. Res.*, 26, 1981, "The Dependence of Soil Penetrometer Pressure on Penetrometer Size", Whiteley et al., pp. 467–476.
*ASAE*, Paper No. 81-1047, 1981, "Moisture and Density Effect on Cone Index", Ayers and Perumpral, pp. 1–15.
*ASAE*, S313.1, Agricultural Engineers Yearbook-1982, "Soil Cone Penetrometer", p. 246.

*Primary Examiner*—Gerald Goldberg
*Assistant Examiner*—Joseph W. Roskos
*Attorney, Agent, or Firm*—Oblon, Fisher, Spivak, McClelland & Maier

[57] ABSTRACT

The apparatus for simulating soil mechanical impedance on the root growth potential attempts to mimic the growth patterns of soil roots. The penetration probe consists of a right conical element attached to a shaft for forcing the conical probe into the soil. The tip of the cone is provided with a plurality of bores which deliver a polymerized carbohydrate lubricant to the cone during soil penetration. This results in a reduction in the axial reaction forces and more accurately mimics the radial growth patterns of plant roots. Moreover, the lubricant mimics lubricants which plant roots naturally exude.

8 Claims, 1 Drawing Figure

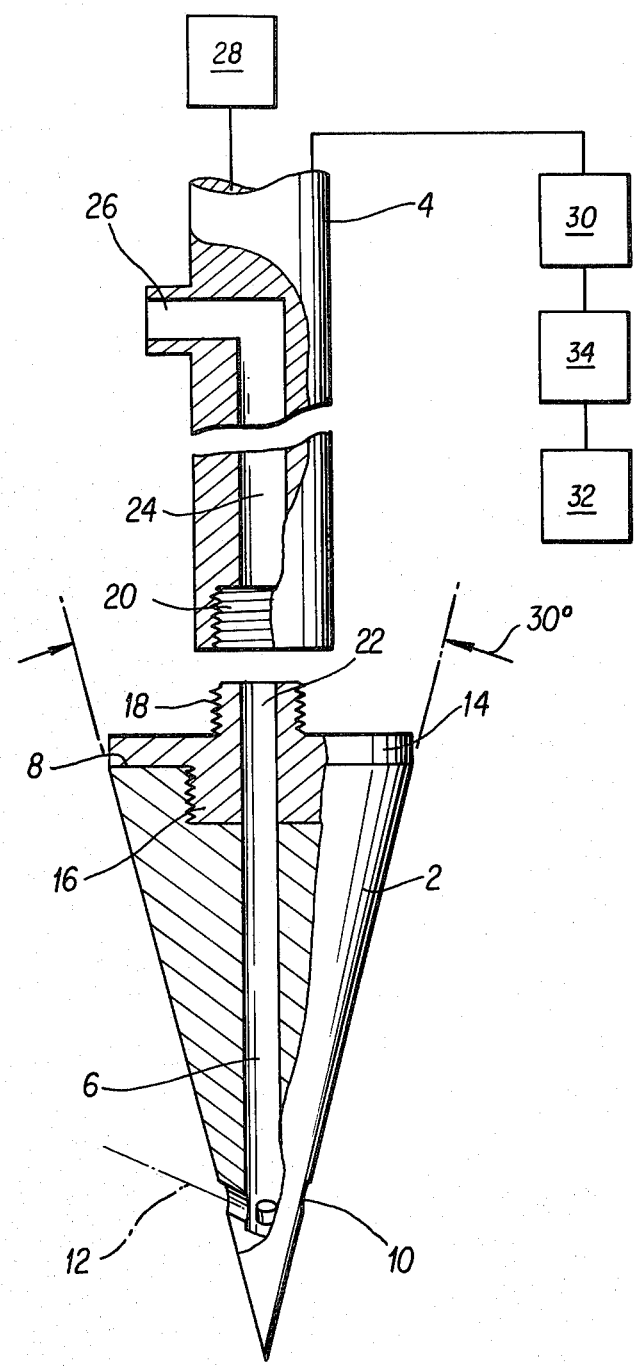

APPARATUS FOR SIMULATING SOIL MECHANICAL IMPEDANCE ON ROOT GROWTH POTENTIAL

BACKGROUND OF THE INVENTION

1. Field of the Invention

The present invention relates to an apparatus for simulating the soil mechanical impedance on the root growth potential of plants. More specifically, the present invention relates to an apparatus for simulating the growth mechanism of natural root systems and for accurately predicting mechanical soil impedance on the growth of these root systems.

2. Description of the Prior Art

Agricultural producers have long recognized that proper soil tilth, adequate water and proper nutrition are essential for crop production. Procedures have long been established for characterizing moisture and nutritional deficiencies, and these procedures have been widely used for addressing problems at the field level. However, procedures for characterizing soil physical conditions relative to root growth potential have lagged. That is, it has in the past been difficult to accurately determine the degree to which the soil physical characteristics will fully or partially inhibit the plant root growth.

Numerous attempts have been made to measure these soil characteristics. On the most primitive level, it has been known to assess such parameters as wheel sinkage or load bearing capacity. More sophisticated parameters for measuring the soil physical conditions included the soil cohesion coefficient, the cone index friction angle and the bulk density. However, not only are these parameters difficult to measure, but they are not fundamentally sound indicators of the forces exerted by a root in the growth process.

The most widely used instrument for ascertaining the mechanical impedance of soil to root growth is the cone penetrometer, one example of which can been seen in U.S. Pat. No. 4,061,021 to Baldwin et al. Such cone penetrometers were developed for use in tillage and trafficability studies, rather than for root penetration impedance studies. However, they have been used in determining root penetration for impedance because of the lack of a more adequate apparatus. It has been found that the cone penetrometers provide sufficient accuracy to predict impedance values which are sufficient to severely inhibit root growth; however, they lack sufficient accuracy to correlate lesser degrees of mechanical impedance with a resulting partial constraint of growing conditions.

SUMMARY OF THE INVENTION

It is therefore an object of the present invention to provide a soil penetrometer which more accurately determines the soil mechanical impedance on root growth potential.

It is another object of the present invention to provide a penetrometer which more accurately simulates the actual growth mechanisms of plant roots.

It is yet another object of the present invention to provide a penetrometer which lubricates the conical surface of the penetrometer.

According to the present invention, the conical surface of the cone penetrometer is supplied with a flow of a lubricant, such as a polymerized carbohydrate lubricant. The lubricant flow is provided by apertures on the conical surface of the cone penetrometer, these apertures being connected to bores in the penetrometer which are in communication with a source of lubricant under pressure. The apertures for providing the lubricant flow are preferably positioned close to the apex of the conical surface of the penetrometer and are equally circumferentially spaced. The bores leading to these apertures are preferably swepted back towards the base of the cone in the radially outward direction so as to avoid clogging of the bores during the penetration of the penetrometer.

The improved operating characteristics of the penetrometer of the present invention are based upon the recognition of the need to simulate or mimic the growth mechanisms of plant roots and the ability of the penetrometer to so simulate these mechanisms. In particular, plant roots grow by extending root hairs into existing pore spaces in the soil, and moving soil particles aside in a radial direction relative to the axis of the root. Near the region of root elongation, a mucigel sheath is present which isolates the root cells from surrounding soil particles. The roots undergo diurnal swelling and shrinkage in the radial direction. Furthermore, a growing root greatly reduces soil-root friction due to the sloughing of cells and the release of polymerized carbohydrates. Thus, two important characteristics of plant root growth are radial soil compression with minimal axial compression, and the reduction in soil-root friction due to cell sloughing and lubricant release.

In contrast, a conventional penetrometer penetrates the soil in gross, complex motions which result in composite soil behavior providing soil failure by a combination of cutting, shearing, compacting and plastic flow of the soil. Under some conditions, dense soil bodies may develop ahead of the penetrometer, effectively changing the geometry of the penetrating system. These soil bodies result in soil-metal friction variability which provides inaccurate readings of the soil conditions. The variability in the soil failure pattern near the tip of the penetrometer has frustrated attempts to develop a general mathematical model applicable to the penetrometer.

The present invention, on the other hand, mimics or simulates the mechanisms which plant roots use during growth, thereby imparting soil displacement patterns which are similar to those imparted by a growing plant root. That is, the provision of a mechanism for supplying a polymerized carbohydrate lubricant to the conical surface of the penetrometer simulates or mimics the cell sloughing and polymerized carbohydrate release of plant roots. Moreover, the resulting reduced friction permits the penetrometer to more closely simulate a plant root's radial expansion. That is, as a conventional penetrometer is forced into the soil, the forces acting upon the soil have both radial and axial components becuase of the soil-metal friction which inhibits the penetrometer from easily sliding downward past the radially moving soil. Thus, the soil is also moved downward with the penetrometer. As mentioned above, the axial components are undesirable since they can cause hardpans and excessive compacting the soil beneath the penetrometer. Moreover, these axial components do not correspond to forces existing during actual plant root growth since the plant root growth is primarily radial.

The lubrication of the conical surface of the penetrometer permits the soil to more easily give way in the radial direction during the penetration of the penetrometer, without being carrying downward by the penetrometer and being compacted therebelow. Thus, the reaction forces to penetration of the penetrometer are to a greater extent radial reaction forces and the mechanisms of a plant root are more accurately simulated according to the present invention.

The apparatus of the present invention thus provides a rapid measure of soil strength. It can accordingly be used in non-agricultural soil engineering applications. In addition, the apparatus of the invention can be used to assess density changes in the root zone, as well as moisture content changes. The simulator could be used with a micro-processor based electronics package allowing for rapid determination of multiple parameters for characterizing the plant root zone.

BRIEF DESCRIPTION OF THE DRAWING

Various other objects, features and attendant advantages of the present invention will be more fully appreciated as the same becomes better understood from the following detailed description when considered in connection with the accompanying drawing and wherein:

FIG. 1 is an exploded elevational view, partially in section, of the apparatus according to the present invention.

DETAILED DESCRIPTION OF THE PREFERRED EMBODIMENT

The present invention will now be described in reference to the accompanying Figure. The penetrometer consists of a right circular cone 2 mounted at one end of a circular shaft 4. The cone 2 is formed of stainless steel and has preferrably a 30° angle of divergence from the apex. A central axial bore 6 extends from the base 8 of the cone to as close to the apex as is practical while retaining strength at the apex of the cone. A plurality of primarily radial bores 10 extend between the surface of the cone and the axial bore 6 at a point as close to the apex of the cone as possible. The axes 12 of the radial bores 10 are swept back. That is, the axes have a slope having the same sense as that of the cone itself.

The cone is preferably provided with an adaptor for connection to the shaft 4. In the embodiment shown, the adpator consists of a stainless steel disc 14 having a projection 16 which threadedly mates with a recess in the base of the cone. The disc 14 also has a projection 18 which is threadedly engageable with a recess 20 of the circular stainless steel shaft 4. The disc 14 is also provided with an axial bore 22 coaxial with the bore 6 of the cone. The cone and disc could be a single element.

The circular shaft 4 includes an axial bore 24 extending into the recess 20 and coaxial with the bore 22 when the disc 14 and the shaft 4 are connected to one another. The bore 24 terminates in an outlet 26 which is connectable to a source of polymerized carbohydrate lubricating liquid under pressure. The source of the lubricating liquid can be conventional, as can the particular liquid itself, and form no part of the present invention. The top of the shaft 4 can be connected to a device 28 for applying axial pressure on the shaft such as the manual device shown in U.S. Pat. No. 4,061,021, a press frame. Appropriate stress measuring devices 30, such as those disclosed in U.S. Pat. No. 3,999,424 can be connected to the top of the rod 4 for measuring the resistance of the ground to penetration by the penetrometer.

In the use of the apparatus of the present invention, the device is transported to a site for soil testing. The source of pressurized lubricant, which can take the form of a tank and pump which are either supported on the shaft 4 or are connected to the outlet 26 by flexible hoses, is activated so that pressurized fluid is supplied to the bores 6, 10 and 24. The penetrometer is then forced into the ground in a conventional manner. During the penetration of the soil, the lubricant being exuded from the bores 10 will cover the conical surface of the penetrometer, thereby reducing the soil-metal friction and minimizing the reaction component in the axial direction. During this penetration, stress sensors 30 mounted on the shaft 4 measure the resistance or impedance of the soil to the penetration of the penetrometer. These measurements can be recorded on a recording device 32 carried by the penetrometer, possibly with processing by a micro-processor 34 which determines a multitude of parameters for characterizing the plant root zone.

The "swept back" orientation of the bores 10 acts to prevent soil from entering and clogging the bores 10 during the penetration step. The positioning of the bores 10 near the apex of the cone insures that a major portion of the cone surface will be covered with the lubricant.

EXAMPLE

Penetration tests were performed on Cecil sandy clay and silica sand using lubricated and non-lubricated penetrometers constructed with cone angles of 15°, 20°, 25° and 30°. The base area for all four cones was 1.29 cm$^2$. The lubricant was exuded from four circumferentially spaced bores such as bores 10 of FIG. 1. The bores in the test cones were positioned about one third of the cone height from the apex of the cone.

The lubricant was a 5% mixture of Nalco TX 270 polymer, manufactured by the Nalco Chemical Company of Chicago, Ill. The mixture was prepared by placing 50 ml of stock polymer solution in a 1000 ml beaker and rapidly filling the volume with tap water. The mixture was stirred vigorously unit a homogeneous solution was obtained. The polymer was delivered to the penetrometer with the aid of a small peristaltic pump at a rate of approximately 18 ml/minute. Lubricant pressure between the pump and the cone was recorded continuously with the aid of a pressure transducer and recorder.

The test penetrometers were attached to a 50 kg load cell mounted in the top stationary cross member of an Instron testing machine. Buckets containing test prepared soil test materials were placed on a platform mounted on the moving cross member. The cross member was moved towards the stationary penetrometer at 480 mm/minute.

The moisture content of the clay and sand test materials ranged from 5 to 20%. During the penetration procedure, penetration was automatically stopped with the cone was about 7 cm from the container bottom, resulting in a penetration depth of 12–15 cm. As a result of these tests, it was found that lubrication reduced the measured forces required for penetration over the entire range of cone angles and soil moisture content. It was found that the lubrication system shown in FIG. 1 was not prone to clogging difficulties. It was also found that the 30° lubricated cone required the least amount of force for penetration.

It was noted in particular that the force necessary for penetration near the bottom of the container was substantial when using non-lubricated penetrometer. This suggests interaction between the penetrometer and the bottom of the container due to soil compaction below the penetrometer as a result of axial forces derived from the movement of the cone. It was further noted that the increase in the soil penetration force necessary near the bottom of the container was substantially reduced for lubricated cones. This suggests a reduction in the interaction between the container bottom and the penetrometer, due to reduced axial reaction forces in the soil. This reduced interaction suggests that lubricated cones might also be useful for studying stratified soils such as those containing fragipans or trafficpans.

Thus, it is possible to provide a consistent soil displacement pattern by use of the lubricated cones of the present invention. A workable mathematical model of the soil penetration accordingly seems possible.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An apparatus for simulating soil mechanical impedance on root growth potential, said apparatus comprising:
   a penetration probe comprising a right conical element having a longitudinal axis;
   means for advancing said probe along said longitudinal axis;
   means for supplying a lubricating fluid to the conical surface of said probe; and
   means for measuring resistance of said probe to movement along said axis.

2. The apparatus of claim 1 wherein said means for supplying a lubricating fluid comprises:
   at least one first axial bore in said probe;
   at least one second bore, each said at least one second bore extending between said first bore and an aperture in said conical surface of said bore; and
   fluid conduit means associated with said means for advancing, said fluid conduit means providing fluid communication between said first bore and a source of pressurized lubricating fluid.

3. The apparatus of claim 2 wherein the axis of the portion of said at least one second bore at said aperture intersects said longitudinal axis of said conical element at a point axially closer to the apex of said conical element than said aperture.

4. The apparatus of claims 2 or 3 comprising four said second bores extending between one said first bore and four of said apertures, said second bores being mutually circumferentially spaced by 90°.

5. The apparatus of claims 2 or 3 wherein said aperture is axially spaced from the apex of said conical element by less than one third of the axial height of said conical element.

6. The apparatus of claims 2 or 3 wherein said means for advancing comprises a rod fixed to the base of said conical element and extending along said longitudinal axis, and wherein said fluid conduit means comprises a third bore in said rod and in fluid communication with said first bore and with a source of pressurized lubricating fluid.

7. The apparatus of claims 2 or 3 wherein said lubricating fluid comprises a polymerized carbohydrate.

8. The apparatus of claim 1 wherein said means for measuring include a mico-processor based electronics package.

* * * * *